United States Patent [19]

Hall

[11] Patent Number: 4,555,383
[45] Date of Patent: Nov. 26, 1985

[54] ELECTROLYTIC CONDUCTIVITY DETECTOR

[75] Inventor: Randall C. Hall, College Station, Tex.

[73] Assignee: O. I. Corporation, College Station, Tex.

[21] Appl. No.: 585,491

[22] Filed: Mar. 2, 1984

[51] Int. Cl.⁴ ............................................. G01N 31/08
[52] U.S. Cl. ...................................... 422/89; 73/23.1; 324/449; 422/90; 422/103; 436/150; 436/161
[58] Field of Search ...................... 422/89, 70, 103, 90; 324/449, 439, 446; 285/342; 436/161, 150; 73/23.1

[56] References Cited

U.S. PATENT DOCUMENTS

| | | | |
|---|---|---|---|
| 3,322,500 | 5/1967 | Sturnberg | 422/89 |
| 3,924,180 | 12/1975 | Salzman et al. | 324/71.1 |
| 3,934,193 | 1/1976 | Hall | 422/89 |
| 4,032,296 | 6/1977 | Hall | 422/89 |
| 4,176,866 | 12/1979 | Rubinstein | 285/342 |
| 4,188,051 | 2/1980 | Burge | 285/342 |
| 4,281,679 | 8/1981 | Stearns | 285/342 |
| 4,295,856 | 10/1981 | Anderson | 422/89 |
| 4,362,994 | 12/1982 | Goldsmith et al. | 324/446 |

OTHER PUBLICATIONS

Perry et al., The *Chemical Engineers' Handbook*, Fifth Edition (1973).
Coulson, D. M., "Electrolytic Conductivity Detector for Gas Chromatography", *Journal of Gas Chromatography* (Apr. 1965), pp. 134–136.
Rhoades, J. W., et al., "Gas Chromatography and Selective Detection of N-Nitrosamines", *Journal of Chromatographic Science*, vol. 8 (Oct. 1970), pp. 616–617.
Jones, P., et al., "Versatile Electrolytic Conductivity Detector for Gas Chromatography", *Journal of Chromatography* 73 (1972), pp. 19–28.
Dolar, J. W., et al., "Selective Detection of Chlorinated Insecticides in the Presence of Polychlorinated Biphenyls", *Journal of the AOAC*, vol. 55, No. 3 (1972), pp. 537–538.

Primary Examiner—Arnold Turk
Attorney, Agent, or Firm—Richards, Harris, Medlock & Andrews

[57] ABSTRACT

A gas chromatograph system is provided with an improved electrolytic conductivity cell (16) for detecting a selected material species in a fluid stream from conventional gas chromatograph (10, 12) having both gas and liquid phases. Planar electrodes (80, 82) are spaced by an insulator (84) and define borehole diameters (88, 90, 92) which enhance the generated signal-to-noise ratio by providing a short fluid transit time within the conductivity detecting volume compared with the effective time of the chromatographic event of interest. A pneumatic damper (108) may be further included to reduce generated system signal noise.

8 Claims, 6 Drawing Figures

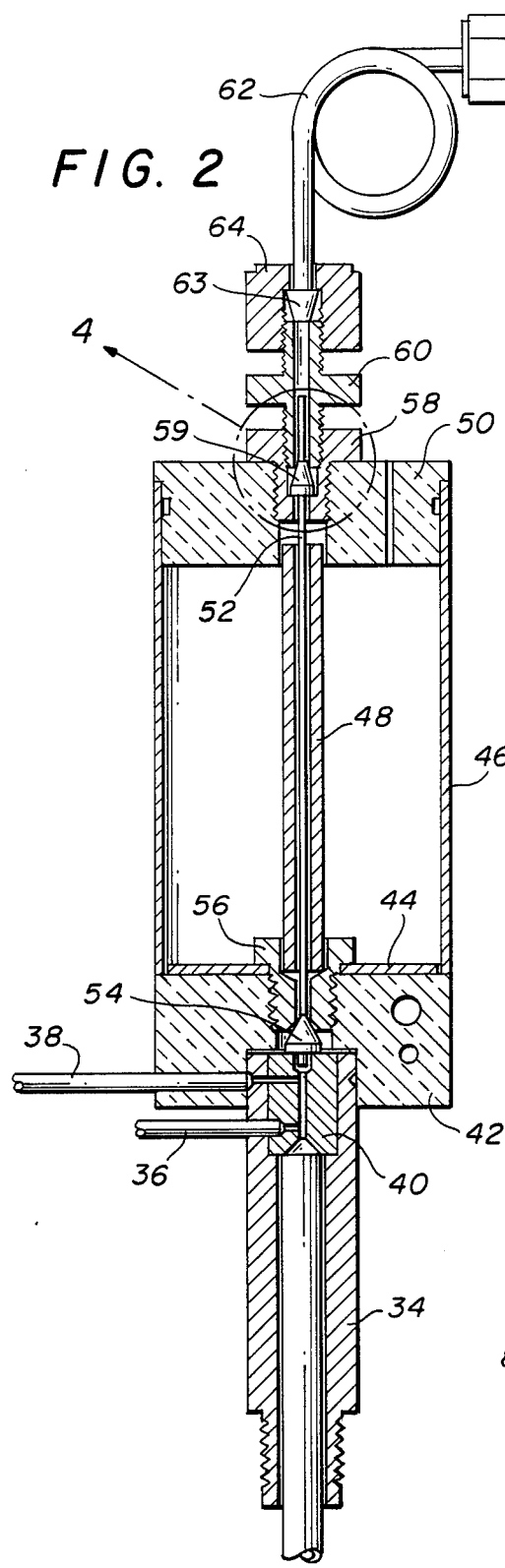
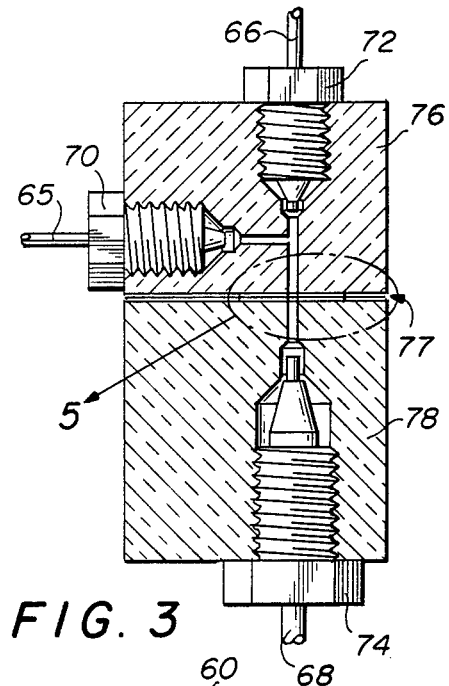
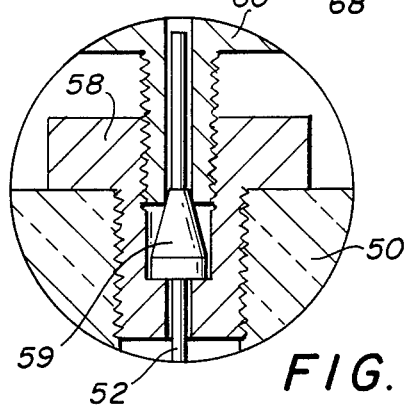
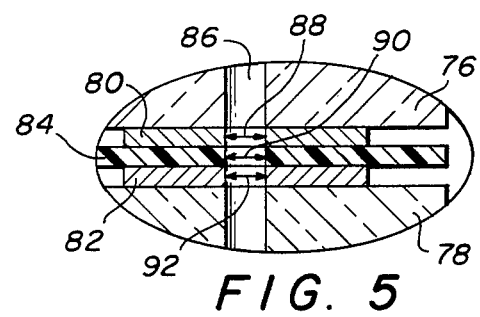
FIG. 2
FIG. 3
FIG. 4
FIG. 5

1

ELECTROLYTIC CONDUCTIVITY DETECTOR

TECHNICAL FIELD

This invention relates to gas chromatography and, more particularly, to an electrolytic conductivity detector for application to a gas chromatography system.

BACKGROUND ART

Chromatography generally involves a separation process for redistributing molecules in a mixture from a thin material phase to a second bulk material phase. The two phases in contact may be liquid-liquid, liquid-solid, vapor-solid or vapor-liquid. Where the bulk phase is a gas stream, the term gas chromatography is used to describe the process. The gas stream is then analyzed to obtain information specific to the transfer molecules. Typical detection systems include thermal conductivity, flame ionization and argon detectors. More recent detectors include electrolytic conductivity detectors providing an electrical signal which is functionally related to the presence of a selected element.

Electrolytic conductivity detectors have long been available for investigating the properties of electrolytes in solutions. Such devices in the prior art typically include electrode surfaces with a continuous phase liquid electrolyte therebetween. Conventional use of electrolytic conductivity detectors in a gas chromatograph system generally follows this prior art approach and separates any gas phase from the liquid phase prior to the detector cell which provides an output related to the electrolyte.

An early typical electrolytic conductivity detector, the Coulson detector, is depicted in the *Journal of Gas Chromatography*, April 1965, at pages 134–137. As therein depicted the electrolytic conductivity detector cell provides a liquid collecting and gas venting section for separating liquid from the gas flow and thereafter introducing the liquid to an electrode volume where the liquid electrolyte is used to form a continuous conductive path between electrode structures in the sidewalls. Yet another electrolytic conductivity detector is depicted in U.S. Pat. No. 3,934,193 to Hall. The Hall detector also separates the flow into a gas flow and a liquid flow and the liquid flow is captured between two concentric electrode surfaces for conductivity measurement. Thus, in both detectors, a slow moving volume of liquid is formed having a relatively long dwell time with respect to chromatographic events.

The Coulson conductivity cell is typically a complex glass device which is difficult to interface with many chromatographs. Further, gases can accumulate in the detector section between electrodes. These gas bubbles can be difficult to displace and the liquid phase tends to merely divert about the gas phase bubble rather than to sweep away the bubble.

The Hall conductivity detector is a substantially more rugged detector and easier to interface than the Coulson detector but the separating chamber is subject to deterioration. The relatively large electrode area per fluid volume ratio produces good sensitivity to the conductivity of the electrolytic fluid but can require frequent cleaning to maintain the volume cleanliness. Thus, it would be desirable to provide an electrolytic conductivity detector which is not subject to blockage by gas accumulation and which is substantially self cleaning, while retaining the large signal-to-noise ratio which is desired for sensitive results.

It will be appreciated that the signal-to-noise ratio can be affected by short term variations in the fluid flow. Such short term variations are typically induced by the pump which moves the solvent liquid, used to dissolve portions of the gas phase, through the system and through the electrolytic conductivity detector. The signal-to-noise ratio could desirably be improved by reducing or eliminating the induced flow fluctuations.

It will also be appreciated that gases evolving directly from the sample being measured are reacted with an oxidant or a reductant to form reaction products suitable for use in combination with an electrolytic conductivity detector. Thus, a reactor is typically furnished having a quartz or nickel reaction tube within a heated volume. Access to the reaction tube is desirable to check for reaction tube cleanliness and tube integrity. However, prior art reactor assemblies generally require removal of the reactor from the analysis system in order to change the reaction tubes. Further, the integrity of the reaction tube is often jeopardized by the system used for supporting the reaction tube within the reactor chamber.

The disadvantages of the prior art are overcome by the present invention, however, and improved apparatus is provided for electrically detecting gas chromatograph products and for enhancing the overall sensitivity of a gas chromatograph with an electrolytic conductivity detection system.

SUMMARY OF INVENTION

In a preferred embodiment of the present invention, a conductivity cell is provided for deriving an output signal which is functionally related to material constituents in a fluid stream having both liquid and gas phases. Apparatus is provided for generating a gas stream from a material sample which is to be analyzed and other apparatus is provided for generating a liquid solvent stream which is effective to separate selected material species from the generated gas stream. A section is provided for mixing the generated gas stream with the solvent stream to form the liquid-gas fluid stream for conductivity analysis. The fluid stream is directed to an electrode assembly having a hole bored through the assembly for receiving the mixed fluid stream and effective to generate an electrical output signal responsive to the selected material species in the liquid solvent phase of the fluid stream.

An objective of the present invention is to directly measure the conductivity of a mixed liquid-gas fluid stream.

Another objective of the present invention is to provide a conductivity detecting path which is not subject to gas bubble blockage.

Yet another objective is to obtain a conductivity measurement region which is substantially self cleaning.

One other objective is to reduce noise signals due to pump action on the solvent.

An objective is to improve access to a reactor tube assembly for reducing the likelihood of reactor tube detriment on system performance.

These objectives and other features and advantages of the present invention will become apparent from the following detailed description, wherein reference is made to the figures in the accompanying drawings.

BRIEF DESCRIPTION OF THE DRAWINGS

FIG. 2 is a cross section of a reactor according to one embodiment of the present invention.

FIG. 3 is a cross section of one embodiment of a detector cell including the present invention.

FIG. 4 is an enlarged cross section showing reaction tube sealing and securing components.

FIG. 5 is a cross section more particularly depicting the electrode system.

DETAILED DESCRIPTION

Figure 1:
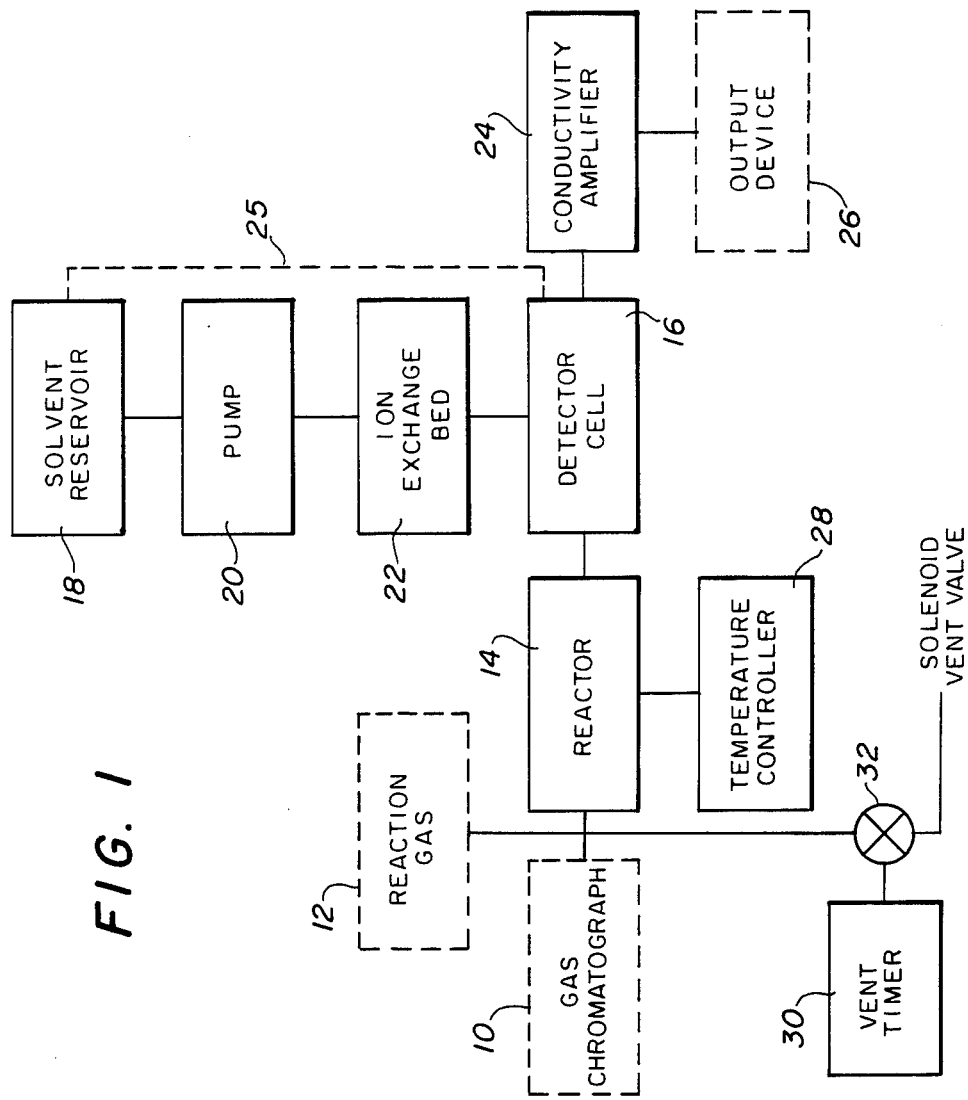
FIG. 1 is a simplified block diagram of a gas chromatograph with an electrolytic conductivity detection system.

Referring first to FIG. 1, there is depicted in block diagram form a gas chromatography system having an electrolytic conductivity detector cell for signal derivation. Gas chromatograph 10 generates a sample gas flow from a selected material within gas chromatograph 10. The output sample gas is combined with reaction gas 12 for input to reactor 14.

The output from reactor 14 generally contains inorganic compounds that will support electrolytic conductivity, such as HCl, $SO_3$, $NH_3$, or $CO_2$. Thus, the reaction gas 12 may be an oxidant or a reductant with respect to the effluent gas from chromatograph 10 to obtain appropriate compounds for the conductivity detector. The gaseous output from reactor 14 is provided to detector cell 16 and combined with a suitable solvent from solvent reservoir 18, as hereinafter described. Detector cell 16 provides a solvent return 25 to solvent reservoir 18 and provides an output signal to conductivity amplifier 24 to obtain an output from device 26.

Solvent may be added to the system from reservoir 18 by the action of pump 20. The solvent may also flow through ion exchange resin bed 22 for solvent purification and removal of extraneous electrically conductive materials prior to reuse. Ion exchange bed 22 is conveniently designed, according to one embodiment of the present invention, to include a pneumatic reservoir for damping pressure and flow changes resulting from the action of pump 20.

The response of detector cell 16 is a function of the product from reactor 14 and the specific solvent from reservoir 18 which are mixed and passed through detector cell 16 to return line 25 for reuse. Further, the output of reactor 14 may be determined by the reaction temperature which is effected by temperature controller 28. The overall gaseous input is further determined by vent timer 30 actuating solenoid vent valve 32 for venting detrimental system gases during a measurement cycle.

Referring now to FIG. 2, there is depicted an improved reactor for use in the present system. Chromatograph input 34 is directed through fluidic valve 40 and combined with reaction gas from entry tube 38. Vent tube 36 is provided for venting solvent which may be passed through chromatographic input 34 at the start of a measurement cycle when vent valve 32 may be actuated. Thus, the desired chromatographic effluent is mixed with the reaction gas at fluidic valve 40 and passed into reaction tube 52.

The reactor shown in FIG. 2 conventionally comprises a base 42, shell floor 44, reactor shell 46 and reactor cap 50. Heating elements (not shown) are included within reactor shell 46 for heating reactor protective core 48 about reaction tube 52. However, an improved sealing and support system is provided for reaction tube 52 to enable tube 52 to be removed by components wholly accessible through cap 50.

Reaction tube 52 is secured at its base by tube fitting nut 56 compressing ferrule 54 and forming a generally leak-tight seal therewith. The ferrule is preferably a reducing ferrule to accommodate a 1/16th inch o.d. reaction tube 52 which can then be removed from the fitting by a small movement of tube fitting nut 56.

The upper reaction tube fitting assembly is more particularly shown in FIG. 4. Reactor tube nut 58 is conveniently formed to threadedly mate with removable ceramic reactor cap 50 to support reaction tube 52. Tube nut 58 is machined to accept ferrule 59 about reaction tube 52 which is sealingly compressed by union 60. In this manner reaction tube 52 is supported and sealed within tube nut 58 wherein relatively fragile 1/16th inch o.d. quartz tubes may form reaction tube 52.

The reactor assembly shown in FIG. 2 may then be connected to an output tube, such as scrubber 62, by the action of tube nut 64 threading on union 60 to sealingly compress ferrule 63. It is readily apparent that the use of reducing ferrules for supporting and sealing about reaction tube 52 and the mating engagement of nuts 56 and 58 with reactor base 42 and reactor cap 50, respectively, permit reaction tube 52 to be easily accessed through removable cap 50 and removed for inspection and/or replacement without removing the entire reactor 14 (FIG. 1) from the system.

The output from reaction tube 52 may be passed to scrubber 62 before passing to reaction product tube 65. Scrubber 62 is optionally provided for removing undesired components of the reacted gas. For example, $SO_2$ and $SO_3$ can be removed by a CaO scrubber; HCl can be removed by a $AgNO_3$ scrubber.

The scrubbed reaction products are then passed by tube 65 to the electrolytic conductivity detector cell shown in FIG. 3. Thus, reaction products are introduced through tube 65 and a selected solvent is introduced through entry tube 66 to meet in upper cell assembly 76. The solvent in tube 66 may be either an aqueous or an organic solvent selected for the materials sought to be detected in the system. As herein used, the term fluid refers to the mixed stream of gas and liquid formed in upper cell assembly 76.

The liquid-gas fluid thus formed passes through electrode assembly 77, generating an output signal, as hereinafter more particularly discussed. The liquid-gas fluid exhausts through tube 68 for return 25 to solvent reservoir 18 (see FIG. 1). Fittings 70, 72 and 74 are conveniently provided to sealingly connect tubes 65, 66 and 68, respectively, to upper cell assembly 76 and lower cell assembly 78.

Electrode assembly 77 (FIG. 3) is more particularly shown in FIG. 5. Flow bore path 86 is provided for the liquid-gas fluid for fluid movement through upper electrode 80, insulator 84 and lower electrode 82. Upper electrode 80 and lower electrode 82 are preferably planar electrodes arranged in a spaced facing relationship with planar insulator 84 therebetween. The fluid in bore path 86 forms a conductive path from upper electrode 80 to lower electrode 82 for transmitting an electrical signal therebetween. As used herein, the terms upper electrode and lower electrode designate the upstream and downstream positions, respectively, in the flow path. Electrodes 80 and 82 and insulator 84 are sealingly clamped between upper cell assembly 76 and lower cell assembly 78 to confine fluid flow through flow bore path 86.

It will be appreciated that the flow through bore path 86 is a liquid-gas mixture, contrary to the teachings of the prior art. It is believed that the planar arrangement of electrodes and insulator with a bore therethrough provides a quite small conductive volume relative to conductive volumes formed in the prior art whereby fluids entering the volume have a short residence time in the effective conductive volume, with a transmit time of about 1 millisecond, compared to the chromatographic event information of interest, typically greater than one second. Momentary fluctuations in the signal from the passage of the mixed liquid and gas phases can be accommodated by conventional electronic filtering and signal processing.

By way of example, a typical measurement volume is $1 \times 10^{-4}$ cubic centimeters and the volumetric flow rates through that volume may typically be 10 to 100 cubic centimeters per minute for the gas phase and 0.1 to 1.0 milliliters per minute for the liquid phase. Thus, the volume is rapidly swept, producing an output signal and maintaining a continuous sweep of the gas phase from the measurement volume to enhance the signal-to-noise ratio.

In one conventional signal processing technique, a bipolar square wave voltage is applied to electrode 80 or electrode 82 and the resulting transmitted signal through the fluid forming the conductive path is detected on the opposed electrode. The signal is processed to filter the undesired capacitive component of the resulting signal from the desired resistive component, the resulting signal is amplified and is provided as an output from electrode assembly 77.

The performance of the electrolytic conductivity detector cell depicted in FIG. 3 was evaluated using an O.I. Corporation Model 610 Total Organic Halogen Analyzer. This unit contains apparatus for sparging volatile halides from water, collecting the liberated halides on an absorbent trap, and thereafter desorbing the absorbed halides. In one instance, the desorbed halides were provided to a separating-type electrolytic conductivity detection cell, such as depicted in U.S. Pat. No. 3,934,193 and the signal-to-noise ratio was compared with the performance of an electrolytic conductivity detection cell as depicted in FIG. 3.

The performance of any gas chromatographic electrolytic conductivity detector depends upon five primary factors: (1) efficiency of formation of the monitored species from the chromatographed compound, (2) efficiency of transport of the monitored species to the detector cell, (3) cell design, (4) stability of the purity and flow rate of the electrolytic conductivity solvent, and (5) conductivity measurement electronics. The formation and transport of the monitored species (HCl) was optimized in the experimental systems and the measurement electronics were standardized to permit an evaluation of the signal-to-noise ratio based solely on cell design. The results of this comparison are presented in table A as follows:

TABLE A

| | BORE DIAMETERS (INCHES) | | | | |
|---|---|---|---|---|---|
| Signal-to-Noise Ratio | Fluid Path 86-Upper | Upper 88 | Insulator 90 | Lower 92 | Path 86-Lower |
| 7–10,000 | .020 | .020 | .020 | .020 | .020 |
| 10–20,000 | .040 | .040 | .020 | .020 | .020 |
| 25–40,000 | .040 | .040 | .030 | .020 | .020 |
| 30–50,000 | .040 | .040 | .040 | .020 | .020 |
| 60–100,000* | .040 | .040 | .030 | .020 | .020 |

*with pneumatic damper

Under the evaluation conditions, the signal-to-noise ratio for the standard prior art system was in the range from 10,000–20,000. It is apparent from Table A that the system herein described obtains a minimum signal-to-noise ratio equal to the ratio obtained from a prior art electrolytic conductivity cell, and generally obtains a superior performance as the electrode design is optimized.

Referring again to FIG. 5, and Table A, the signal-to-noise ratio has been determined as a function of the upper electrode bore diameter 88, insulator bore diameter 90 and lower electrode bore diameter 92. The test results indicate that improved results are obtained with upper electrode bore diameter 88 and insulator bore diameter 90 the same dimension and with lower electrode bore diameter 92 reduced. The results also indicate that a pneumatic damper in the solvent delivery system 18, 20, 22, (FIG. 1) can further improve the results.

Figure 6:
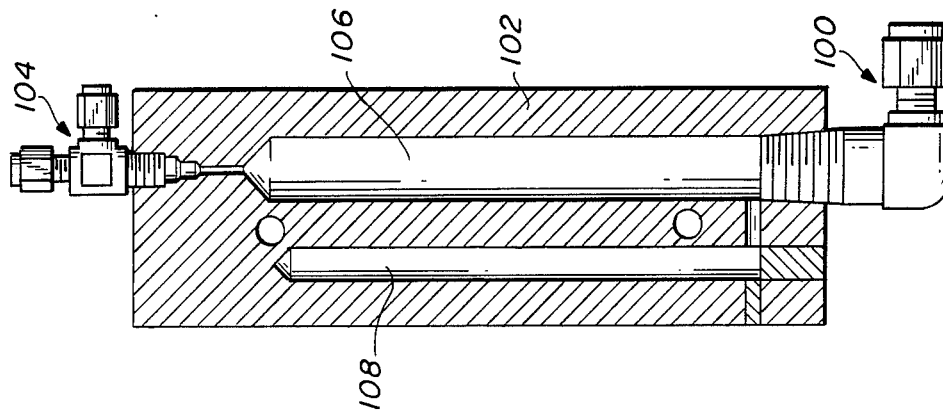
FIG. 6 depicts one embodiment of a pneumatic damper.

Referring now to FIG. 6, there is depicted one embodiment of a pneumatic damper incorporated with ion exchange bed 22 (FIG. 1). Solvent entry fitting 100 generally directs solvent flow within resin cartridge 102 through ion exchange resin reservoir 106 to outlet fitting 104. Pneumatic damper reservoir 108 provides a pressurized chamber for accommodating pressure and flow fluctuations during the action of pump 20 (FIG. 1). Pneumatic damper reservoir 108 reduces the short-term flow pulsations normally associated with small gear pumps and reciprocating pumps. Pneumatic damper reservoir 108 is conveniently contained within resin cartridge 102, but might be provided as a separate pressurizer-type unit.

The application of pneumatic damper reservoir 108 with the embodiment of the electrolytic conductivity detector according to the present invention produces the enhanced results depicted in Table A. However, the use of a pneumatic damper reservoir may have application to any pumped solvent delivery system used with electrolytic conductivity detection cells already existing in the prior art for use in gas chromatography.

It is therefore apparent that the present invention is one well adapted to attain all of the objects and advantages herein above set forth together with other advantages which will become obvious and inherent from the description of the apparatus itself. It will be understood that certain combinations and subcombinations are of utility and may be obtained without reference to other features and subcombinations. This is contemplated by and is within the scope of the present invention.

As many possible embodiments may be made of this invention without departing from the spirit or scope thereof, it is to be understood that all matters herein set forth in the accompanying drawings are to be interpreted as illustrative and not in any limiting sense.

What is claimed is:

1. A chromatographic system having a conductivity cell for deriving an output signal functionally related to a throughput fluid, comprising:

chromatographic means for generating a gas stream from a material sample, means for generating a solvent stream effective to separate selected material species from said gas stream, means for mixing said gas stream with said solvent stream to form a mixed gas-liquid phase stream of a throughput fluid and for passing the throughput fluid to an electrode assembly without gas-liquid separation, and an electrode assembly for continuous axial flow of said mixed gas-liquid phase stream of said throughput fluid, having spaced first and second planar electrodes transverse to said axial flow and defining respective first and second boreholes for said axial flow of said mixed phase stream wherein an electrical output signal is obtained across said first and second electrodes during passage of said mixed phase stream axially through said boreholes.

2. Apparatus according to claim 1, wherein said second borehole has a diameter less than said first borehole.

3. Apparatus according to claim 1 or 2, wherein said means for generating a solvent stream further includes: a pneumatic damper for reducing spurious flow induced signal noise from said mixed phase fluid stream.

4. Apparatus according to claim 3, wherein said means for generating a gas stream further includes:

a reactor having a removable cap, a reaction tube within said reactor, and compression fitting means for securing and supporting said reaction tube within said reactor, said compression fitting means interfacing with said reactor and said removable cap in manner effectively permitting removal and replacement of said reaction tube by removal of said removable cap.

5. Apparatus according to claim 4, wherein said compression fitting means further comprises:

a reactor tube nut receiving said reaction tube and threadedly engaging said removable cap, a first compression ferrule engaging a top portion of said reaction tube within said reactor tube nut, a compression fitting threadedly engaging said first reactor tube nut and compressing said first ferrule to sealingly engage said reaction tube, a second compression ferrule engaging a bottom portion of said reaction tube adjacent a sealing surface within said reactor, and a compression tube nut accessible when said removable cap is removed from said reactor and about said reaction tube and threadedly engaging a base portion of said reactor adjacent said sealing surface for sealing said second ferrule about said reaction tube and against said sealing surface.

6. In a combined chromatography system and electrolytic conductivity cell deriving an output signal from a chromatographic event, the combination comprising a gas chromatograph for generating a sample gas, a reactor chamber for reacting said sample gas with a selected reaction gas to form an input gas, a supply of solvent for separating a selected material from said input gas, a tube for mixing said input gas and said solvent to form a mixed phase fluid stream and for passing said mixed phase fluid stream to a conductivity cell without gas-liquid separation, and a conductivity cell for continuous axial flow of said mixed phase fluid stream having spaced first and second planar electrodes transverse to said axial flow and defining respective first and second boreholes for said axial flow of said mixed phase fluid stream, said first and second boreholes cooperating with said spaced electrodes to define a measurement volume effective for said axial flow of said fluid to transit in a time substantially less than a time defining said chromatographic event to derive said output signal across said first and second electrodes defining said first and second boreholes.

7. In the combination of claim 6, wherein said second borehole has a diameter less than said first borehole.

8. In the combination of claim 6 or 7, further including:

means effective to pneumatically damp said fluid stream for reducing spurious flow induced signal noise from said mixed phase fluid steam.

* * * * *